US005772581A

United States Patent [19]
Gaines

[11] Patent Number: 5,772,581
[45] Date of Patent: Jun. 30, 1998

[54] PENLIGHT LARYNGOSCOPE

[76] Inventor: James F. Gaines, 25339 Rainbow La., Chantilly, Va. 20152

[21] Appl. No.: 837,210

[22] Filed: Apr. 22, 1997

[51] Int. Cl.$^6$ ...................................................... A61B 1/06
[52] U.S. Cl. .......................... 600/190; 600/197; 600/199; 600/243
[58] Field of Search .................................. 600/190, 191, 600/197, 199, 212, 243, 247, 241

[56] References Cited

U.S. PATENT DOCUMENTS

| | | | |
|---|---|---|---|
| 2,648,329 | 11/1953 | Morch | 600/107 |
| 3,507,272 | 4/1970 | Laerdal | 600/191 |
| 3,598,113 | 8/1971 | Moore | 600/199 |
| 3,771,514 | 11/1973 | Huffman | 600/191 |
| 3,856,001 | 12/1974 | Phillips | 600/199 |
| 3,916,881 | 11/1975 | Heine | 600/212 |
| 4,037,588 | 7/1977 | Heckle | 600/191 |
| 4,114,609 | 9/1978 | Moses . | |
| 4,226,228 | 10/1980 | Shin et al. . | |
| 4,295,465 | 10/1981 | Racz | 600/199 |
| 4,344,419 | 8/1982 | Burgin . | |
| 4,425,909 | 1/1984 | Rieser | 600/197 |
| 4,566,439 | 1/1986 | Burgin | 600/212 |
| 5,065,738 | 11/1991 | Van Dam . | |
| 5,178,132 | 1/1993 | Mahefky | 600/199 |

FOREIGN PATENT DOCUMENTS 612116  11/1948  United Kingdom .................. 600/199

*Primary Examiner*—Richard J. Apley
*Assistant Examiner*—Ira Hatton
*Attorney, Agent, or Firm*—C. J. Husar, Esq.

[57] ABSTRACT

The disclosure relates to a penlight laryngoscope which is particularly useful by veterinarians in the examination of many animals. It finds use in long nosed animals as well as smaller animals such as squirrels, rabbits and other small species. The penlight is removable from the instrument permitting autoclave sterilization. The instrument includes a barrel portion for receiving the light source, a middle blade portion which has a concave surface and a flat terminal end portion. The concave portion provides a reflective surface to illuminate the area under examination and also adds strength to the blade. The flat terminal end has tapered sides which permit the pushing aside of the cheeks of small animals for examining their molars. The penlight laryngoscope also finds use in the examination of humans.

8 Claims, 1 Drawing Sheet

PENLIGHT LARYNGOSCOPE

BACKGROUND OF THE INVENTION

1. Field of the Invention

The present invention relates generally to a laryngoscope. More specifically, it relates to a penlight laryngoscope.

The penlight laryngoscope will be used in place of wooden, metal or plastic tongue blades, battery operated laryngoscopes with detachable blades and fingers to depress the tongue and epiglotis of dogs, cats, goats, sheep, horses, laboratory animals, birds and other species for the purpose of inserting endotracheal tubes and/or other devices into the trachea and esophagus. It will also be used to depress tissues in the pharyngeal area for the purpose of examination and surgery and other manipulations in the region.

The penlight laryngoscope can also be used to push aside cheeks of rabbits, guinea pigs, chinchillas, hamsters and other animals in order to examine their molar teeth, tongues and cheek tissues and to perform surgery and other manipulations of these organs.

The penlight laryngoscope is designed to be used one-handed so as to allow the other hand free to manipulate instruments and other devices. The light source is a disposable penlight and fits tightly into the barrel portion of the device and includes a control switch which is readily accessible and can be depressed with the thumb or finger. However, other battery operated penlights may be used as well. Extending forward of the barrel portion is a blade portion which is slightly concave to provide rigidity, better reflect and concentrate light, and to prevent the casting of any shadow as would occur with a totally flat blade. Extending forward of the concave blade portion is a flat terminal end portion which tapers to a rounded terminal end. This flat portion extends for only a short distance and is provided to allow the user to direct the blade where it is needed to move the epiglotis or cheeks aside. The use of a flat portion at the terminal end does not produce any shadows as a uniformly flat blade while at the same time it adds strength and rigidity to the blade.

2. Brief Description of the Prior Art

Presently, the other devices currently used for the above described procedures have numerous short comings. For example, wooden, plastic and metal tongue blades need an additional hand to hold the point light source or else some other source of bright light is needed. In many cases they are not rigid enough to depress the tongue or other oral tissues of a larger animal. Some of these devices are too large to place into the cheek area of small rodents and rabbits.

The type of laryngoscope used in humans (battery containing handle with a detachable lighted curved blade) is very difficult to use in animals other than certain dogs with short jaws and cats. The blade is too short to be used in long nosed dogs or in large animals. The human device is too unwieldy for application in rodents and other small species.

The otoscope that many veterinarians use to examine rodent and rabbit molars is minimally effective. When used in an awake animal, the creature will bite on the plastic cone of the otoscope and block it with the tongue and food debris.

Some of the known prior devices are as follows: U.S. Pat. No. 4,114,609 issued to John A. Moses is directed to a laryngoscope blade which is attachable to a handle which is disposed at a right angle to the blade and requires awkward hand movements for its use. U.S. Pat. No. 4,226,228 issued to Shin et al is directed to a multiple joint retractor which comprises a flexible, segmented blade with a handle disposed perpendicular to the blade. U.S. Pat. No. 4,344,419 issued to Kemit Burgin discloses another tongue depressor having a handle positioned at a right angle to the blade member. A second embodiment discloses an in-line flashlight and depressor. However, the blade is formed of plastic with a downward curved portion and is attached to a conventional large diameter flashlight. U.S. Pat. No. 5,065,738 issued to David J. Van Dan is directed to a laryngoscope blade sheath. The purpose of the sheath is to protect a patient's mouth, teeth, tongue and throat during examination.

None of the above cited patents, taken alone or in combination, disclose a compact, readily controlled examining device of the type disclosed by the subject invention.

SUMMARY OF THE INVENTION

The subject invention provides a convenient, readily managed examining instrument which finds use in the examination of many different animals and also has application with humans. It is especially useful in long nosed larger animals as well as smaller animals. It provides for single-hand use while permitting the other hand to be free to perform other manipulations.

OBJECTS OF THE INVENTION

It is a principal object of the invention to provide a convenient examination instrument which serves many useful functions in the examination of animals.

It is another object of the invention to provide an examination instrument which includes a user friendly, small diameter barrel portion for receiving a penlight.

Yet another object of the invention is to provide an examination instrument which permits shadow-free observation of an organ under examination.

It is a further object of the invention to provide an instrument which is autoclavable without the light source in place and will withstand hot and cold sterilization procedures.

Still another object of the invention is to provide an instrument which is of sufficient length and strength to permit laryngeal examination and/or allow for easy insertion of an endotracheal tube or endoscopic instruments into the esophagus.

An additional object of the invention is to provide an improved examination instrument for the purposes described which is inexpensive, dependable and fully effective in accomplishing its intended purposes.

These and other object of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENT

Figure 1:
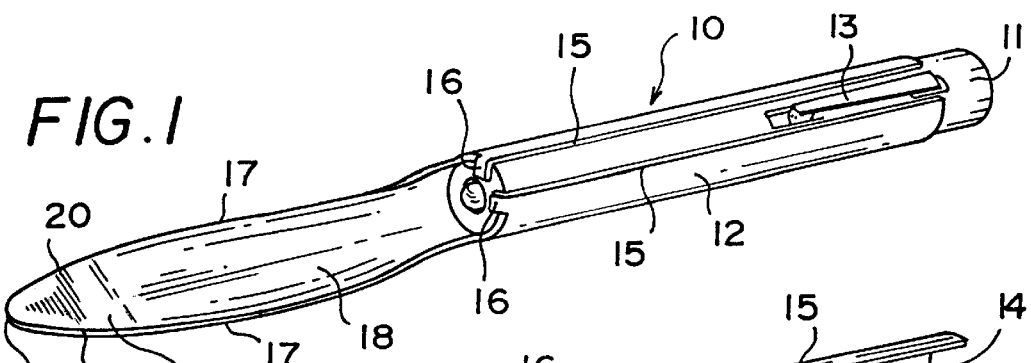
FIG. 1 is a perspective view of the invention, with the penlight received in the barrel portion.

Turning now to FIG. 1 of the drawings, there is shown a perspective view of the penlight laryngoscope indicated by the reference numeral 10 and having a longitudinal axis X-X. As shown, penlight 11 has been snugly received in barrel portion 12 with on-off switch 13 projecting through a slot 14 formed by a pair of spaced edges 15 for easy access by the user. The forward end of barrel portion 12 is provided with a pair of downwardly turned tabs 16 which serve as an abutment or stop member for retaining penlight 11 in barrel portion 12.

The penlight 11 which is used is a commercially available penlight wherein the on/off switch is located in the clip which would secure the penlight in the user's pocket. The barrel portion 12 is provided with a slot 14 to receive the on/off switch 13 which is conveniently located when the penlight 11 is inserted into the barrel portion 12. Forward of barrel portion 12 is an integral middle blade portion 17 which has a concave surface 18. Immediately forward of middle blade portion 17 is end portion 19 having two sides 20 which taper inwardly to the centerline and form a rounded terminal end as shown at 21. The length of the terminal end is approximately 0.500 inches, barrel portion 12, middle portion 17 and terminal end portion 19 are made of a non-corrosive metal and made by a laser cutting process of a flat blank sheet of material and subsequently stamped to form the barrel portion and concave middle portion. An advantage of laser cutting the blank metal material is the fact that the resultant edges of the blade are smooth and do not require any further time consuming sanding or finishing as would be the case if the flat blank material were stamped or punched. Although the preferred material is stainless sheet material, 304 SS, other suitable materials such as plastic or polymers may be acceptable. However, the plastic materials may not be autoclavable.

Figure 2:
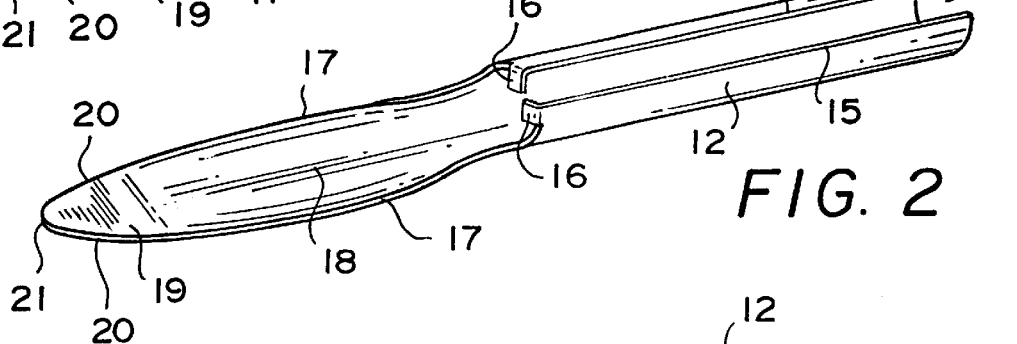
FIG. 2 is another perspective view of the invention without the penlight mounted therein to reveal the internal details thereof.

FIG. 2 is a perspective view similar to that of FIG. 1. However, in this view, penlight 11 has been removed to provide a better illustration of the examining instrument per se. There are three portions which make-up the examining instrument i.e. an elongated barrel portion 12, middle blade portion 17 and a forward end portion 19. As indicated above, the elongated barrel portion 12 receives disposable penlight 11 and includes a slot 14 through which on/off switch 13 of the penlight 11 protrudes for ready finger access. Middle blade portion 17 is the primary working portion of the examining instrument. It includes a smooth under surface, side edges 17 and a concave upper surface 18 to permit pressure contact to be made with the tongue, inner cheeks and epiglotis without any injury to these areas. The concave surface 18 provides a reflective surface for illuminating the area with shadow-free light while end portion 19 can be used for moving the epiglotis and other structures aside during examination of the pharyngeal and laryngeal areas.

Figure 3:
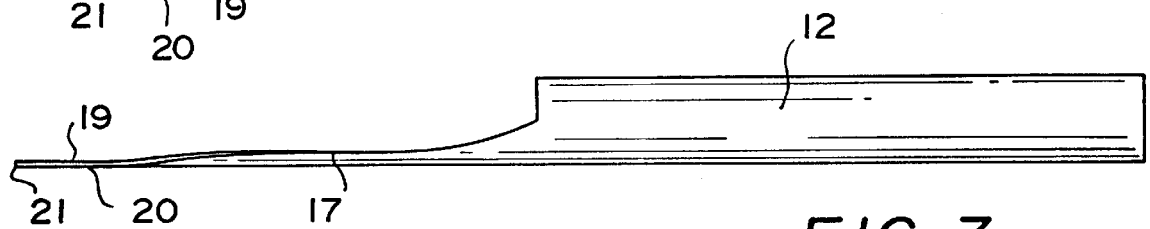
FIG. 3 is a side view of the invention without the penlight therein, showing the curvature and flat portions of the blade.

FIG. 3 is a side view illustrating the barrel portion 12, middle blade portion 17 and terminal end portion 19. The overall length of the device is approximately 7.345 inches including the barrel portion 12 of approximately 3.900 inches and middle blade portion 17 and terminal end portion of 3.445 inches. Middle blade portion 17 is approximately 0.650 inches at its widest point, tapering to a rounded end portion 21 of approximately 0.284 inches. The internal diameter of the barrel portion 12 is approximately 0.530 inches. As illustrated, it can be seen that the middle blade portion 17 is a continuation of barrel portion 12, thus providing additional thereto.

Figure 4:
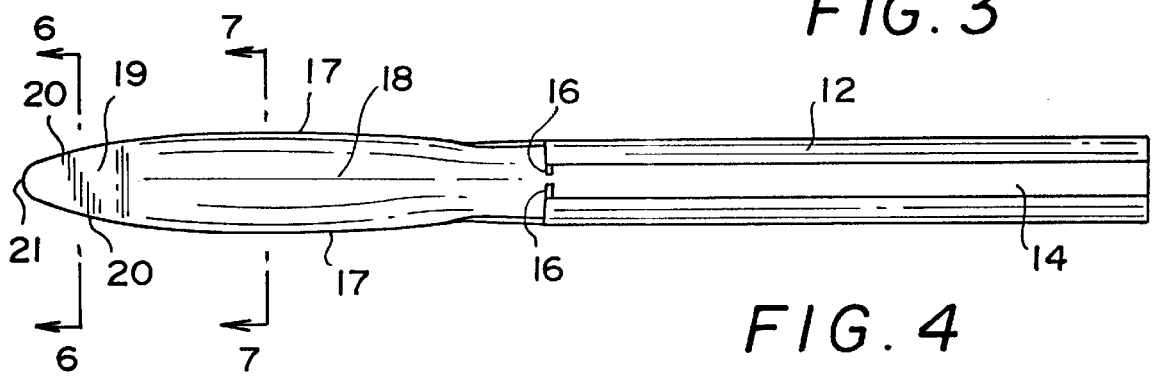
FIG. 4 is a plan view of the invention, illustrating the curvature and tapered forward portion of the blade.

FIG. 4 is a plan view of the penlight laryngoscope 10 with penlight 11 removed.

Figure 5:
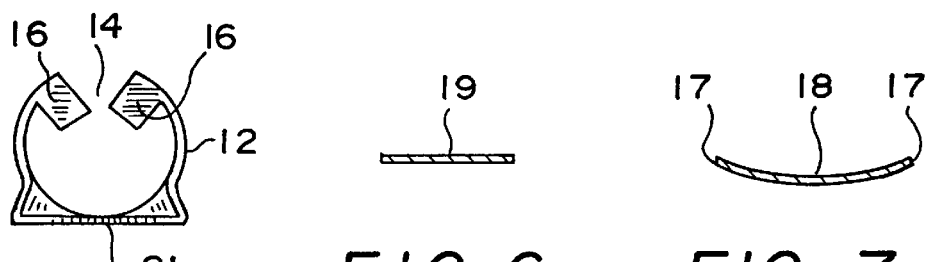
FIG. 5 is a frontal view of the invention, illustrating the curvature of the penlight holder and the front tab retainers.

FIG. 5 is a frontal end view showing the barrel portion 12 and the retaining tabs 16.

Figure 6:
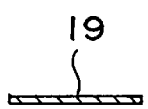
FIG. 6 is a sectional view, taken along the lines 6—6 of FIG. 4, illustrating the flat portion of the blade.

FIG. 6 is a sectional view taken along the line 6—6 of FIG. 4, showing the flat surface of terminal end portion 19.

Figure 7:
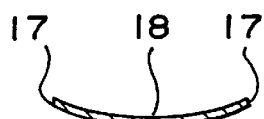
FIG. 7 is also a sectional view, taken along the lines 7—7 of FIG. 4, illustrating the slight curvature of the blade.

FIG. 7 is a cross-sectional view, taken along the line 7—7 of FIG. 4, showing the slightly concave surface 18 of middle portion 17.

While the invention has been described in its preferred embodiment, it is to be understood that the words which have been used are words of description rather than limitation and that changes may be made within the purview of the appended claims without departing from the full scope or spirit of the invention.

Having thus described my invention, I claim:

1. An in-line unitary illuminated laryngoscope and examining instrument comprising:

an in-line unitary examining instrument and removable lighting means;

said in-line unitary examining instrument including a first generally cylindrical barrel portion having a first open end and a second oppositely disposed end with stop means thereon and a centrally located slot extending the full length of said first generally cylindrical barrel portion for receiving and retaining said removable lighting means;

a second arcuate blade portion extending forward from said second end of said first generally cylindrical barrel portion and having a slight concave curvature facing upwardly along its upper surface; and a third flat portion integral with and extending forward from said second arcuate blade portion a short distance forming the terminal end thereof with each of said first, second and third portions in axial alignment and having a common longitudinal axis;

whereby said illuminated laryngoscope can be manipulated by one hand of the user to depress a tongue, expand cheeks, and displace an epiglotis while illuminating the oral cavity and directing light to the larynx while performing an examination or manipulation.

2. An in-line unitary illuminated laryngoscope as defined in claim 1 wherein said stop means of said first generally cylindrical barrel portion serves to retain said removable lighting means therein.

3. An in-line unitary illuminated laryngoscope as defined in claim 2 wherein said removable lighting means is a cylindrical disposable penlight which conforms to said first generally cylindrical barrel portion and is received therein.

4. An in-line unitary illuminated laryngoscope as defined in claim 3 wherein said stop means comprises a plurality of inwardly turned tabs extending from said first generally cylindrical barrel portion which engage the forward portion of said disposable penlight when inserted therein and serves to retain said disposable penlight therein.

5. An in-line unitary illuminated laryngoscope as defined in claim 1 wherein said concave surface of said second arcuate blade portion is opaque and provides a reflective surface to illuminate the oral cavity and provide a shadow-free view of the larynx.

6. An in-line unitary illuminated laryngoscope as defined in claim 1 wherein said third portion comprises a flat forward tapering opaque portion extending a short distance with both sides tapering inwardly toward its centerline and having a smooth rounded terminal end for displacing the epiglotis to permit a shadow-free view of the larynx.

7. An in-line unitary illuminated laryngoscope as defined in claim 2 wherein said removable lighting means is a commercially available penlight with an on/off switch and replaceable batteries.

8. An in-line unitary illuminated laryngoscope as defined in claim 7 wherein said centrally located slot receives said on/off switch of said penlight when said penlight is inserted into said first generally cylindrical barrel portion thus providing convenient access by the user.

* * * * *